US009990741B2

United States Patent
Panin

(10) Patent No.: US 9,990,741 B2
(45) Date of Patent: Jun. 5, 2018

(54) MOTION CORRECTION IN A PROJECTION DOMAIN IN TIME OF FLIGHT POSITRON EMISSION TOMOGRAPHY

(71) Applicant: Siemens Medical Solutions USA, Inc., Malvern, PA (US)

(72) Inventor: Vladimir Y. Panin, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 38 days.

(21) Appl. No.: 15/268,968

(22) Filed: Sep. 19, 2016

(65) Prior Publication Data
US 2017/0091963 A1   Mar. 30, 2017

Related U.S. Application Data

(60) Provisional application No. 62/233,726, filed on Sep. 28, 2015.

(51) Int. Cl.
*H05G 1/26* (2006.01)
*H05G 1/62* (2006.01)
(Continued)

(52) U.S. Cl.
CPC ............ *G06T 11/005* (2013.01); *A61B 6/037* (2013.01); *A61B 6/4417* (2013.01);
(Continued)

(58) Field of Classification Search
CPC ...... G06T 11/005; G06T 11/00; G06T 11/003; G06T 11/008; G06T 7/207; G06T 7/20;
(Continued)

(56) References Cited

U.S. PATENT DOCUMENTS

| 2005/0253074 A1* | 11/2005 | Jones | G01T 1/2985 |
| | | | 250/363.04 |
| 2006/0163485 A1* | 7/2006 | Stearns | G01T 1/2985 |
| | | | 250/363.03 |

(Continued)

OTHER PUBLICATIONS

C. Tsoumpas, J.E. Mackewn, P. Halsted, A.P. King, C. Buerger, J.J. Totman, T. Schaeffter, and P.K. Marsden, "Simultaneous PET—MR acquisition and MR-derived motion fields for correction of non-rigid motion in PET," Ann. Nucl. Med., vol. 24, pp. 745-770, 2010.

(Continued)

*Primary Examiner* — Vincent Rudolph
*Assistant Examiner* — Stephen Brinich

(57) ABSTRACT

Motion correction is performed in time-of-flight (TOF) positron emission tomography (PET). Rather than applying motion correction to reconstructed images or as part of reconstruction, the motion correction is applied in the projection domain of the PET data. The TOF data from the PET scan is altered to account for the motion. The TOF data is altered prior to starting reconstruction. The motion in the patient or image domain is forward projected to provide motion in the projection domain of the TOF data. The projected motion of different phases is applied to the TOF data from different phases, respectively, to create a combined dataset of motion corrected TOF data representing the patient at a reference phase. The dataset is larger (e.g., similar size from projection data dimension point of view, but contains more counts per projection data unit or is more dense) than available at one phase of the physiological cycle and is then used in reconstruction.

19 Claims, 3 Drawing Sheets

(51) Int. Cl.
G06T 11/00 (2006.01)
A61B 6/03 (2006.01)
A61B 6/00 (2006.01)

(52) U.S. Cl.
CPC .......... *A61B 6/5205* (2013.01); *A61B 6/5247* (2013.01); *A61B 6/5264* (2013.01); *A61B 6/4266* (2013.01); *G06T 2207/10088* (2013.01); *G06T 2207/10104* (2013.01); *G06T 2207/20221* (2013.01); *G06T 2207/30004* (2013.01); *G06T 2211/412* (2013.01)

(58) Field of Classification Search
CPC ......... G06T 7/215; G06T 7/223; G06T 7/231; G06T 7/238; A61B 6/037; A61B 6/032; A61B 6/4417; A61B 6/5205; A61B 6/52; A61B 6/5247; A61B 6/5241; A61B 6/5264; A61B 6/5258
USPC ..... 382/130–132, 107, 236; 378/4–8, 21–27, 378/901; 250/363, 363.01–363.05
See application file for complete search history.

(56) References Cited

U.S. PATENT DOCUMENTS

| | | | |
|---|---|---|---|
| 2010/0086101 A1* | 4/2010 | Thielemans | G01T 1/1647 378/21 |
| 2010/0303319 A1* | 12/2010 | Wang | G06T 11/006 382/131 |

OTHER PUBLICATIONS

F. Qiao, T. Pan, J.W. Clark, and O.R. Mawlawi, "A motion-incorporated reconstruction method for gated PET studies," Phys. Med. and Bio., vol. 51, p. 3769, 2016; Abstract Only.
S. Matej, S. Surti, S. Jayanthi, M.E. Daube-Witherspoon, R.M. Lewitt, and J.S. Karp "Efficient 3-D TOF PET reconstruction using view-grouped histo-images: DIRECT—direct image reconstruction for TOF," IEEE Trans. Med. Img., vol. 28, pp. 739-751, 2009.
Y. Li, M. Defrise, S.D. Metzler, and S. Matej, "Transmission-less attenuation estimation from time-of-flight PET histo-images using consistency equations," Phys. Med. Bio. vol. 60, p. 6563, 2015; Abstract Only.
K. Thielemans, C. Morel, M.W. Jacobson, J.H. Kaempf, and S. Mustafovic "Normalisation of Histogrammed List Mode Data," IEEE Trans. Nucl. Sci., vol. 55, pp. 543-551, 2008.
V.Y. Panin, A.M. Smith, J. Hu, F. Kehren and M.E. Casey, "Continuous bed motion on clinical scanner: Design, Data Correction and Reconstruction", Phys. Med. Bio., vol. 59, pp. 6153-6174, 2014.
W.P. Segars, G. Sturgeon, S. Mendonca, J. Grimes, and B.M.W. Tsui, "4D XCAT phantom for multimodality imaging research," Med. Phys., vol. 37, pp. 4902-4915, 2010.
N.A. Karakatsanis, H. Zaidi, and C. Tsoumpas, "Generalized 3D and 4D motion compensated whole-body PET image reconstruction employing nested EM deconvolution," In Imaging Systems and Techniques (IST), 2014 IEEE International Conference on, pp. 263-268, 2014.
I. Hong, J. Judson, and M.E. Casey, "Ultrafast Elastic Motion Correction via Motion Deblurring," Nuclear Science Symposium and Medical Imaging Conference, Seattle, WA, M10-97, 2014.
F. Gigengack, L. Ruthotto, M. Burger, C.H. Wolters, X. Jiang, and K.P. Schafers, "Motion correction in dual gated cardiac PET using mass-preserving image registration," IEEE Trans. Med. Img., vol. 31, pp. 698-712, 2012.
C. Liu, L.A. Pierce, A.M. Alessio, and P.E. Kinahan, "The impact of respiratory motion on tumor quantification and delineation in static PET/CT imaging," Phys. Med. Bio., vol. 54, p. 7345, 2009; Abstract Only.
S. Vandenberghe, M.E. Daube-Witherspoon, R.M. Lewitt, and J.S. Karp, "Fast reconstruction of 3D TOF PET data by axial rebinning and transverse mashing," Phys. Med. Biol., vol. 51, p. 1603, 2006.
B. Bai, Y. Lin, W. Zhu, R. Ren, Q. Li, M. Dahlbom, F. DiFilippo, and R.M. Leahy. "MAP reconstruction for Fourier rebinned TOF-PET data." Phys. Med. and Bio., vol. 59, p. 925, 2014; Abstract Only.
I. Polycarpou, C. Tsoumpas, and P.K. Marsden, "Analysis and comparison of two methods for motion correction in PET imaging," Med. Phys., vol. 39, pp. 6474-6483 2012.
M. Defrise, V.Y. Panin, and M.E. Casey, "New consistency equation for time-of-flight PET," IEEE Trans. Nucl. Sci., vol. 60, pp. 124-133, 2013.
S.A. Nehmeh, Y.E. Erdi, T. Pan, A. Pevsner, K.E. Rosenzweig, E. Yorke, G.S. Mageras, H. Schoder, P. Vernon, O. Squire, H. Mostafavi, S.M. Larson and J.L. Humm "Four-dimensional (4D) PET/CT imaging of the thorax," Med. Phys., vol. 31, pp. 3179-3186, 2004.
F. Büther, M. Dawood, L. Stegger, F. Wübbeling, M. Schäfers, O. Schober, and K.P. Schäfers "List mode-driven cardiac and respiratory gating in PET," J. Nucl. Med., vol. 50, pp. 674-681, 2009.
W. van Elmpt, J. Hamill, J. Jones, D. De Ruysscher, P. Lambin, and M. Öllers, "Optimal gating compared to 3D and 4D PET reconstruction for characterization of lung tumours," Eur. J. Nucl Med. Mol. Imag., vol. 38, pp. 843-855, 2014.
Y. Picard and C.J. Thompson, "Motion correction of PET images using multiple acquisition frames," IEEE Trans. Med. Img., vol. 16, pp. 137-144, 1997.
T. Li, B. Thorndyke, E. Schreibmann, Y. Yang, and L. Xing, "Model-based image reconstruction for four-dimensional PET," Med. Phys., vol. 33, pp. 1288-1298, 2006; Abstract Only.
F. Qiao, T. Pan, J.W. Clark, and O.R. Mawlawi, "A motion incorporated reconstruction method for gated PET studies," Phys. Med. Bio., vol. 51, pp. 3769-3783, 2006; Abstract Only.
F. Lamare, M.J.L. Carbayo, T. Cresson, G. Kontaxakis, A. Santos, C.C. Le Rest, A.J. Reader, and D. Visvikis, "List-mode-based reconstruction for respiratory motion correction in PET using non-rigid body transformations," Phys. Med. Bio., vol. 52, p. 5187, 2007.
M. Dawood, F. Büther, X. Jiang, and K.P. Schäfers, "Respiratory motion correction in 3D PET data with advanced optical flow algorithms," IEEE Trans. Med. Img., vol. 27, pp. 1164-1175, 2008.

* cited by examiner

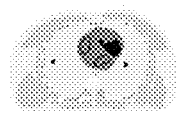
FIG. 5A
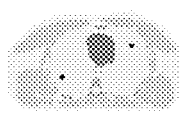
FIG. 5B
FIG. 5C
FIG. 5D
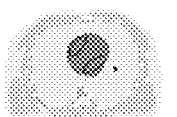
FIG. 5E
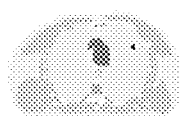
FIG. 5F
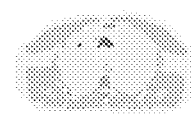
FIG. 5G
FIG. 5H
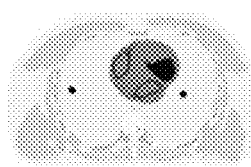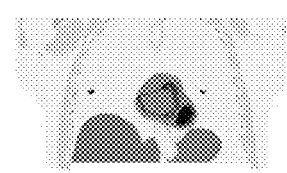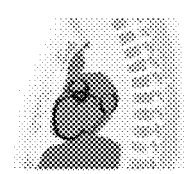
FIG. 6A
FIG. 6B
FIG. 6C
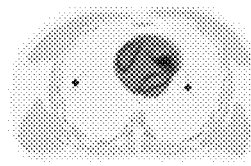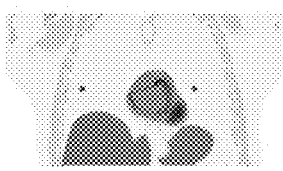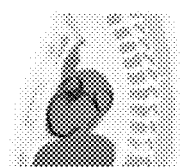
FIG. 6D

MOTION CORRECTION IN A PROJECTION DOMAIN IN TIME OF FLIGHT POSITRON EMISSION TOMOGRAPHY

RELATED APPLICATIONS

The present patent document claims the benefit of the filing date under 35 U.S.C. § 119(e) of Provisional U.S. Patent Application Ser. No. 62/233,726, filed Sep. 28, 2015, which is hereby incorporated by reference.

BACKGROUND

The present embodiments relate to positron emission tomography (PET). PET acquisition requires scans of long duration, and a significant magnitude of patient motion during the scan is sometimes unavoidable. For example, the pattern caused by breathing may result in a relatively large displacement of organs and consequent blurring of clinically relevant PET features in regions affected by the motion.

To limit the effects of motion, the PET data is separated by phases of the breathing cycle. The breathing pattern may be monitored either by external devices or by tracing the movement of objects in the list mode file domain of the PET data. Once the breathing pattern is established, PET data is separated into gates according to the phase or amplitude of respiration. Each gate represents a particular (quasi) frozen phase of motion. The gate with minimally integrated motion is chosen to reconstruct the PET image. While the motion artifact is suppressed, image quality suffers from a greater amount of noise due to reconstruction from less than all the PET data.

To achieve motion artifact suppression and approach maximum signal-to-noise ratio (SNR), each gate's data is individually reconstructed and registered to one of the reconstructions in the image domain. The aligned reconstructions (or images from the reconstructions) are then averaged. Another approach is to reconstruct one image from all available data through the incorporation of the field of motion into the reconstruction process (i.e., repeated each iteration of the reconstruction or in the forward and backward projection loop). This approach is fairly computationally extensive and also requires assessment of the motion phase for correction factors, such as attenuation.

BRIEF SUMMARY

By way of introduction, the preferred embodiments described below include methods, systems, and non-transitory computer readable media for motion correction in time-of-flight (TOF) PET. Rather than applying motion correction to reconstructed images or as part of reconstruction, the motion correction is applied in the projection domain of the PET data. The TOF data from the PET scan is altered to account for the motion. The TOF data is altered prior to starting reconstruction. The motion in the patient or image domain is forward projected to provide motion in the projection domain of the TOF data. The projected motion of different phases is applied to the TOF data from different phases, respectively, to create a combined dataset of motion corrected TOF data representing the patient at a reference phase. The dataset is larger (in signal, not necessarily in size) than available at one phase of the physiological cycle and is then used in reconstruction.

In a first aspect, a method is provided for motion correction in time-of-flight positron emission tomography. A motion vector field for motion of tissue of a patient over a plurality of phases of a physiological cycle is acquired from a memory. A positron emission tomography (PET) scanner having a plurality of detectors acquires time of flight data along lines-of-response from emissions. The time of flight data is in a plurality of sets for the respective plurality of phases. The motion vector field is forward projected along at least one dimension. The time of flight data for the plurality of phases is combined as a function of the forward projection of the motion vector field. An image is reconstructed from the combined time of flight data from the plurality of phases and displayed.

In a second aspect, a non-transitory computer readable storage medium has stored therein data representing instructions executable by a programmed processor for motion correction in time-of-flight positron emission tomography. The storage medium includes instructions for correcting time of flight data of a patient for motion of the patient, reconstructing an activity distribution from the motion corrected time of flight data, and displaying a positron emission tomography image as a function of the activity distribution.

In a third aspect, a system is provided for motion correction in time-of-flight positron emission tomography (PET). Rings of detectors spaced axially are configured to perform a PET scan along lines of response between the detectors. A coincidence processor is configured to detect the lines of response and time of flight for events acquired from the PET scan. A processor is configured to apply motion correction to data representing the detection of the lines of response and time of flight and to reconstruct an activity distribution from the motion corrected data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 5A-D show example axial PET images for one gate, FIG. 5D shows an example coronal PET image for the one gate, FIGS. 5E-G show example axial PET images for another gate, and FIG. 5H shows an example coronal PET image for this other gate; and FIGS. 6A-D show reconstructed axial, coronal, and sagittal PET images with image-based motion correction, no motion correction, TOF motion correction with 580 ps resolution data, and TOF motion correction with 290 ps resolution data.

DETAILED DESCRIPTION OF THE DRAWINGS AND PRESENTLY PREFERRED EMBODIMENTS

Non-rigid motion correction is performed on time of flight (TOF) data. TOF data may be considered to be histogram images (histo-images). Non-rigid motion correction may be performed in this quasi-image space rather than in image or object space or as a parameter in reconstruction. The locality property (i.e., location based property of line of response (LOR) further parameterized by TOF) of TOF data is used to locally perform motion correction. The motion is approximated as locally rigid on a scale of TOF resolution. Data correction factors, such as normalization and attenuation, are also combined for motion compensation depending on the combination of data. The benefit of the presented motion correction is that only one data set needs to be used for the final reconstruction and that one dataset includes data from different phases of a physiological cycle without causing the extent of blurring resulting from a lack of motion correction.

The motion correction is approximate in nature, since fine sampling in the TOF direction is not feasible at currently existing TOF resolutions. Nevertheless, the potential degradation in image quality may be compensated by TOF redundancy in both the azimuthal and axial directions. The motion vector field representing the motion is difficult to precisely estimate at high resolutions. The benefit of motion correction in the TOF projection space as compared to image-based motion correction is that only one data set, corrected for motion, needs to be reconstructed to achieve higher SNR.

Figure 1:
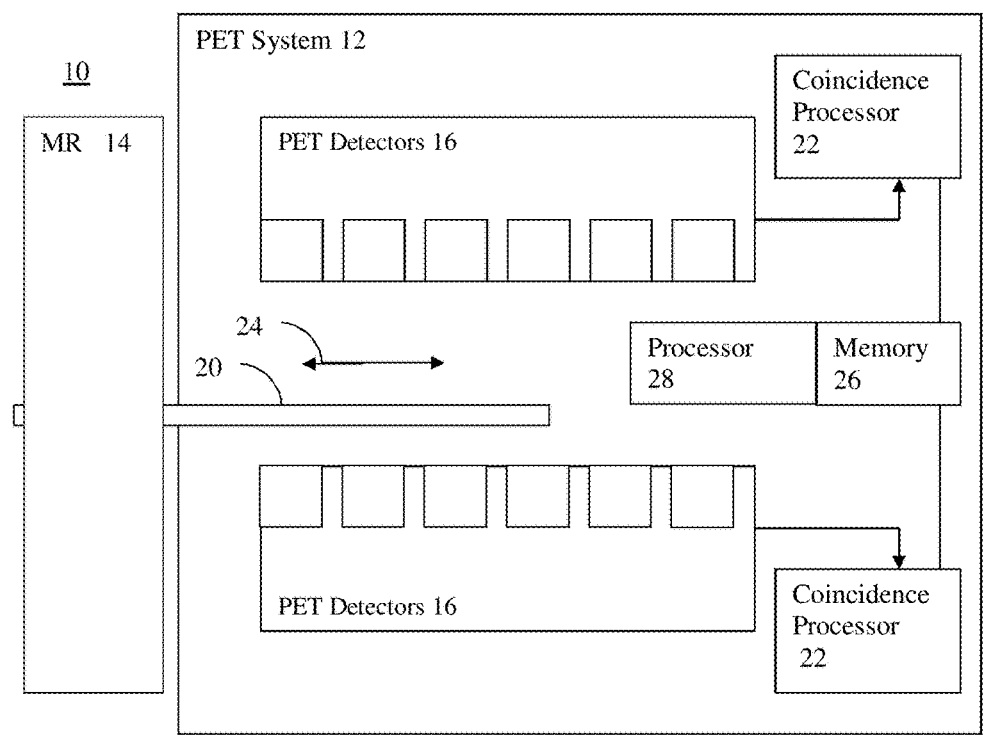
FIG. 1 is a block diagram of a system, according to one embodiment, for motion correction in TOF PET.

FIG. 1 shows a medical system 10 for motion correction in TOF PET. The medical system 10 implements the method of FIG. 3 or other methods. Motion correction is applied in projection space or the TOF data domain rather than during reconstruction or between reconstructed images in the image or object domain.

The medical system 10 includes a magnetic resonance (MR) scanner 14 and PET system 12. In other embodiments, the medical system 10 includes a computed tomography (CT), ultrasound, optical (e.g., camera), or other type of scanner. In yet other embodiments, the medical system 10 does not include any other imaging modality than the PET system 12, at least used for motion correction.

The MR scanner 14 includes local coils, a whole body coil, and/or gradient coils positioned in a magnetic field of a main coil. The MR scanner 14 is within a same housing as the PET system 12 or is spaced apart by and connected by a common track for the bed 20. Completely separate MR scanner 14 and PET system 12 may be used.

The MR scanner 14 measures magnetic resonance response from a patient on the bed 20 or on a different bed. The processor 28 or a different processor computes one or more motion vector fields from the response. By measuring tissue response at different times to change in spins induced by radio frequency pulses, the motion of the tissue between those times may be calculated. Other sources of the motion vector field may be provided, such as determining motion based on PET data, a model, or empirical study.

The PET system 12 includes rings of detectors 16, a bed 20, coincidence processors 22, a memory 26, and a processor 28. The processor 28, memory 26, and/or a display are part of the PET system 12 or are separate (e.g., a computer or workstation). Additional, different, or fewer components may be provided. For example, the system is a computer without the detectors 16 and bed 20, instead relying on data acquired by a separate scanner. As another example, the medical system 10 includes power supplies, communications systems, and user interface systems.

The bed 20 is a gurney, table, or other support to hold an examination subject, such as a patient. A robot, gears, cable, track, rollers, and/or other device move or allow movement of the bed 20. The movement is along an axial dimension represented by double arrow 24. In alternative embodiments, the bed 20 is fixed relative to the detectors 16. Continuous bed motion, discrete bed motion, or no bed motion may be used. The detectors 16 and/or PET scanner 10 form a bore or hollow cylinder through which the bed 20 holds or moves the patient. The distance from the axial axis of this bore is the radial distance. The angle about the axial axis is the azimuth. Other coordinate systems, such as a cylindrical or polar coordinate system, may be used.

The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

Figure 2:
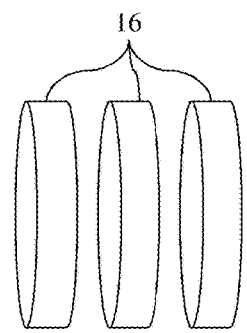
FIG. 2 shows example rings of detectors.

The detectors 16 are arranged individually or in groups. Blocks or groups of detectors 16 are arranged in any pattern around the bore. FIG. 2 represents blocks of detectors 16 arranged as separate rings around the bore. The rings are shown spaced apart, but are placed adjacent or abutting each other. Any gap may be provided between blocks within a ring, detectors within a block, and/or between rings. Any number of detectors in a block (e.g., 8 or 16), detector blocks in a ring, and/or rings may be used. The rings may extend completely or only partially around the bore.

The PET system 12 is a nuclear imaging system. The detectors 16 are used to perform a PET scan along LOR between the detectors 16. The detectors 16 detect gamma rays emitted indirectly by a positron-emitting tracer. Pairs of gamma rays generated by a same positron may be detected using the ring of the detectors 16. The pairs of gamma rays travel about 180 degrees apart. If the direction of travel intersects the arrangement of detectors 16 at two locations, a coincident pair may be detected. To distinguish specific pairs, the coincidence of detected gamma rays is determined. The timing of receipt is used to pair the detected gamma rays. The timing, as prompt data, also indicates the time of flight, providing information about where along a LOR the emission occurred. This TOF data is parameterized by LOR and time defining location along the LOR, providing a histogram-image of distribution of emissions by location (LOR and position along LOR).

Each individual detection output from the detectors 16 includes energy, position, and timing information. Alternatively, the detectors 16 output energy information and a receiving processor determines the timing and position (e.g., based on port assignment or connections). The timing information is used to determine coincidence of detection by different detectors by the coincidence processors 22 as well as general position along the LOR of the emission. Pairs of gamma rays associated with a same positron emission are determined by the coincidence processors 22. Based on the detected event, the LOR and TOF is determined, given the detectors involved in the detection of that event.

The coincidence processors 22 and/or the processor 28 categorize the detected events relative to a physiological cycle. For example, a breathing cycle is divided into any number (e.g., 8) of phases. Based on the time of occurrence relative to a breathing cycle measured with the sensor or from the TOF data, counts for each bin (e.g. location along each LOR) are maintained separately for each phase. Each event is assigned to one of the histogram images or datasets of detected events for the phases. The counts or events are gated to the physiological cycle. Since the detection of each event is along a LOR, the TOF data is in a projection domain. The uncertainty of the location of the emission along the range, even with the prompt data, results in the TOF data representing a projection.

The detected events are passed to the memory 26 and/or processor 28. The processor 28 connects with the detectors 16, such as through the coincidence processors 22. The processor 28 also connects with the MR scanner 14 and/or memory 26 to receive motion information.

The processor 28 is a general processor, digital signal processor, graphics processing unit, application specific integrated circuit, field programmable gate array, digital circuit, analog circuit, combinations thereof, or other now known or later developed device for processing TOF data, motion correcting TOF data, forward projecting motion data, motion correcting normalization factors, motion correcting attenuation, and/or reconstructing. The processor 28 is a single device, a plurality of devices, or a network. For more than one device, parallel or sequential division of processing may be used. Different devices making up the processor 20 may perform different functions, such as one processor for handling motion correction in the projection domain and another processor for reconstructing the object (i.e., patient) space. In one embodiment, the processor 28 is a control processor or other processor of the medical system 10 or the PET system 12. In other embodiments, the processor 28 is part of a separate workstation or computer.

The processor 28 operates pursuant to stored instructions to perform various acts described herein. The processor 28 is configured by software, firmware, and/or hardware to perform acts 58, 59, and 62-66 of FIG. 3. The operation and configuration of the processor 28 is first described in general below. The method, as well as theory behind the operation, is described in more detail in the following discussion of FIG. 3.

The processor 28 is configured to apply motion correction to data representing the detection of the LOR and TOF (together the TOF data). The motion correction is applied in the projection domain to the TOF data prior to use in reconstruction. The motion correction accounts for motion between the phases. The motion is forward projected into an event or projection domain. This forward projected motion is then used to rebin or estimate the location of the event as if the motion did not occur between the phases (i.e., alter the TOF data to be for another LOR and/or time-based position along the LOR).

The processor 28 may be configured to perform other motion correction. For example, measures of attenuation from different times or phases are motion corrected and averaged. As another example, normalization coefficients or factors accounting for efficiency for detection along each line of response are motion corrected.

After the TOF data for the various phases is motion corrected to a reference phase, the processor 28 is configured to reconstruct an activity distribution from the motion corrected TOF data. The combined counts from the different phases, after motion correction, are used to reconstruct. The reconstructed data provides a representation of the events in an image or object domain, such as activity in tissue represented by Cartesian coordinates.

The processor 28 generates an image from the reconstructed activity distribution. A slice or planar image for an arbitrary plane may be generated, such as an image for axial, coronal, and/or sagittal planes. A three-dimensional rendering may be performed on the reconstructed activity distribution, such as using projection, surface, path tracing, or other volume rendering.

For processing, the TOF data bypasses the memory 26, is temporarily stored in the memory 26, or is loaded from the memory 26. For example, the processor 28 uses the events (e.g., TOF data) stored in the memory 26 for processing, so loads the TOF data from the memory 26.

The TOF data (e.g., sinograms), phase information, attenuation information, normalization information, motion vector field, projection of the motion, motion corrected data, reconstructed image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 12 or a remote workstation or database, such as a PACS memory.

The memory 26 is additionally or alternatively a non-transitory computer readable storage medium with processing instructions. The memory 26 stores data representing instructions executable by the programmed processor 28 for motion correction in time-of-flight positron emission tomography. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 12 may include a display. For example, the processor 28 reconstructs the patient or object being scanned from the TOF data. The reconstruction is used for three-dimensional rendering, multi-planar reconstruction, or two-dimensional imaging of the function of the tissue of the patient. The images are displayed on the display. The display is a CRT, LCD, plasma screen, projector, printer, or other output device for showing an image.

Figure 3:
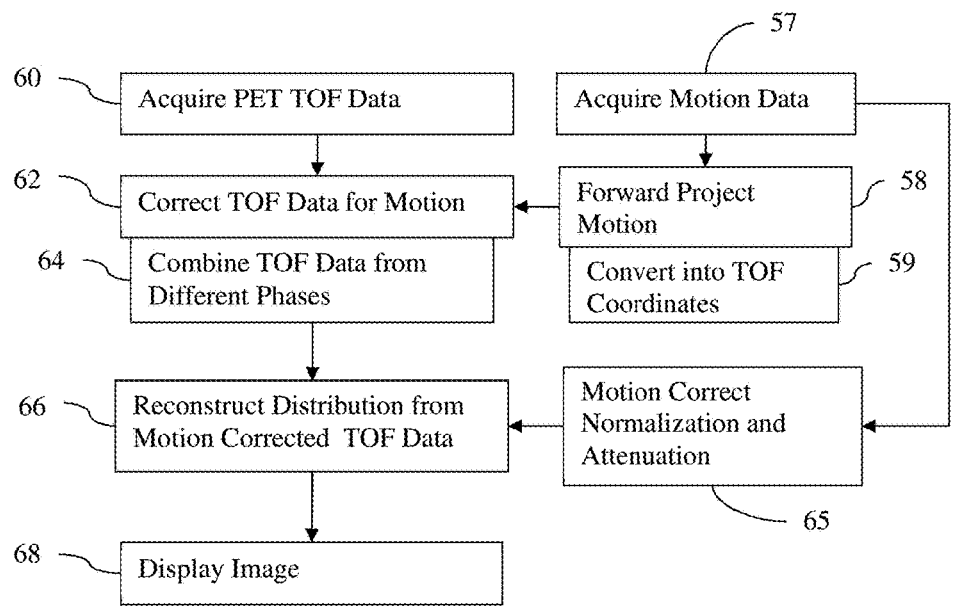
FIG. 3 is a flow chart of an embodiment of a method for motion correction in TOF PET.

FIG. 3 shows a method for motion correction in time-of-flight positron emission tomography. Motion is projected into the projection space or TOF domain. By motion correcting the TOF data, the detected counts from different phases may be combined into a larger dataset, allowing a single reconstruction with less noise as compared to separate reconstruction for different phases and image-based motion correction between images for those different phases.

The method of FIG. 3 is implemented by the processor 28, the PET system 12, the medical system 10, and/or other component or system. For example, the PET system 12 implements act 60, and the MR scanner 14 implements act 57. The display implements act 68. Other acts are performed by the processor 28 or another processor.

Additional, different, or fewer acts may be performed. For example, act 68 and/or act 65 are not performed. The acts are performed in the order shown or a different order. Acts 57-59 may be performed prior to, at a same time as, or after act 60. As another example, act 65 may occur before, after or in parallel with any of acts 58, 59, 62, and 64.

In act 57, a motion vector field for motion of tissue of a patient over a plurality of phases of a physiological cycle is acquired from memory. Alternatively, the motion vector field is acquired by processing data or from another device. For example, magnetic resonance imaging acquires data directly measuring the motion at each of different times or acquires data representing tissue at different times that may be processed to determine the motion between the different times.

The motion vector field indicates the direction and amplitude of motion at different locations, such as locations distributed in three-dimensions at a same grid or resolution as the TOF data. For each location, the motion vector represents motion along three Cartesian coordinates, but other coordinate systems may be used.

The motion for each phase of the physiological cycle is determined. The motion over time or between phases is provided. For example, with the TOF data grouped between eight phases, the motion between each of the phases in sequence is measured. The motion throughout the physiological cycle of tissue is provided, loaded, and/or calculated. The motion for each phase is relative to the preceding phase or total motion from a reference phase.

Estimating the field of motion or motion vector field (MVF) from a breathing sensor is a challenging task since the non-rigid model includes a displacement vector for each image voxel at each phase. This is an underdetermined problem, and additional constraints, such as spatial smoothness, are typically exploited. Motion estimation from a breathing sensor or detection of the physiological cycle is sensitive to the image noise and typically has a non-unique solution. In a hybrid modality imaging, such as a PET MRI and PET CT, the motion may be estimated from the higher signal-to-noise imaging modality (e.g., MR or CT). The TOF data may be used to find the motion. Since TOF data (histogram images) are distributed across azimuthal and polar angle samples, consistency conditions, likely in local format, that interconnect the TOF samples, are used.

For motion correction in TOF projection space, the motion in the object space is converted or transformed into the projection space. In act 58, the motion is forward projected. The TOF modeled projection data may be considered as image blurring by TOF kernel h (e.g., a Gaussian model). An example representation of the projection, p, is:

$$p(r, t, z, \phi, \theta) = \int_{-\infty}^{\infty} dl f(r\vec{e}_r + l\vec{e}_t + z\vec{e}_z) h(t - l), \quad (1)$$

where three unit vectors are:

$$\vec{e}_r = \{\cos\phi, \sin\phi, 0\}$$

$$\vec{e}_t = \{-\cos\theta \sin\phi, \cos\theta \cos\phi, \sin\theta\}$$

$$\vec{e}_z = \{0,0,1\} \quad (2)$$

$f(\vec{x})$ is the emission distribution in object space, r and $\phi$ are 2D sinogram coordinates, t is the TOF coordinate (i.e., time of flight defining location along the LOR), z is the axial coordinate of the midpoint of the LOR, unit vector $\vec{e}_t$ defines the LOR direction, and $\theta$ is the co-polar angle between the LOR and a transaxial plane. Explicit notations of $\phi$ and $\theta$ are not used as motion correction is performed for their fixed values.

The TOF data is separated by gating from the physiological cycle, resulting is different sets of histogram images. The gates and corresponding histogram images are denoted by time index m. There is a connection between the target image and the motion-deformed image through motion matrix, M, given as:

$$M^m(\vec{x}; \vec{x}') ; f(\vec{r}) = \int d\vec{r}' M^m(\vec{r}, \vec{r}') f^m(\vec{r}') \quad (3),$$

where $\vec{r} = r\vec{e}_r + t\vec{e}_t + z\vec{e}_z$ are used instead of $\vec{x}$, and $M^m$ is rescaled according to the Jacobian of variable transformation (inverse of $\cos\theta$). Other representations may be used.

Assuming that motion is approximately commutative with a relatively narrow TOF blurring kernel (the relation is exact when the TOF kernel is a delta function), the motion matrix is given as:

$$M^m(r,t,z;r',t'',z')h(t''-t') \approx M^m(r,t'',z;r',t',z')h(t-t') \quad (4),$$

and a motion relationship in the modeled TOF projection space is given as:

$$p(\vec{r}) = \int d\vec{r}' M^m(\vec{r}; \vec{r}') p^m(\vec{r}') \quad (5).$$

In act 58, a processor calculates the motion matrix in the projection space. The forward projection integrates the motion from the object space of the tissue into the projection space along the LORs of the TOF data. This forward projection and following correction of act 62 occurs before reconstruction of the tissue or object. The forward projection and following correction of act 62 are used to correct the TOF data in the projection space or TOF domain.

The motion vector field is forward projected along one or more dimensions, such as forward projection along three Cartesian coordinates of the motion vector field in the object space. Motion displacement or the motion vector field for one phase or gate relative to another is represented as:

$$d(x) = \{d_x(x), d_y(x), d_z(x)\} \quad (6).$$

This representation has three component images: motion along each coordinate x, y, and z. The motion images of each dimension are forward projected. Alternatively, the forward projection is performed for the three dimensions for one motion image.

The forward projection is performed in a manner similar to how modeled projection data are obtained from an activity image. The forward projection operator from any reconstruction technique may be used. The projection of the emission distribution to the TOF domain approach is used to project the motion into the TOF domain. In one embodiment, the motion vector field, MFV, has three components, what is displacement along each spatial dimension. Each component is essentially an image of the same size as the activity image. Therefore, forward projection is the same procedure on each component as in the case of the activity image projection data generation. Forward projection is performed three times due to used 3D spatial domain.

In act 59, the forward projections along the Cartesian coordinates are converted into radial coordinate, time, and axial coordinate system of the TOF data. The TOF data to be motion corrected is not in the Cartesian coordinate system, so the forward projected motion is converted into the coordinate system of the TOF data. Any or no conversion may be used depending on the coordinate systems for the motion and the TOF data.

The sampling of the displacement field is the same as for TOF data. In other embodiments, up sampling, down sampling, decimation, interpolation, extrapolation, nearest neighbor assignment and/or other process is used to deal with unequal sampling of the motion and the TOF data. The proper smoothing of the displacement field by a TOF kernel is ensured. The motion vector field "projection data" is represented as:

$$d(rtz) = \{d_x(rtz), d_y(rtz), d_z(rtz)\} \quad (7)$$

for a given $\phi$ and $\theta$ are converted into (r,t,z) displacements. The motion as projected into the TOF or projection domain and converted to the same coordinate system may be used to motion correct TOF data.

In act 60, a PET scanner or system uses a plurality of detectors to acquire TOF data along lines-of-response from emissions. The projection data along lines of response is acquired with a time coordinate to indicate the general location along the line at which the emission occurred. PET sinogram data is acquired. TOF data for emissions detected along a plurality of LORs is acquired. The acquisition is by scanning with the PET scanner with a plurality of detectors. In alternative embodiments, the acquisition is by transfer or upload from a memory.

Gamma rays are detected by one or more rings of detectors or other grouping of detectors. The patient ingests or is injected with a radiopharmaceutical. The radiopharmaceutical includes an isotope and gathers at tissue of interest. The isotope decays over time, resulting in generation of a positron. More emissions occur at the tissue of interest due to binding of the radiopharmaceutical and/or absorption of the tissue of interest.

LOR events from a patient are detected. The PET scanning acquires detected emission events for functional information. The detected gamma rays are checked for coincidence to define LORs, and the time difference or relative timing for coincident detections is recorded as prompt data. Any time window may be used for coincidence processing, such as 0.2 microsecond coincidence time window. Each detected emission event corresponds to a line or part of a line through a patient. By detecting emission events from different angles around a patient, a volume may be reconstructed.

The acquisition occurs over any period. For example, the acquisition is over 1, 10, 100, or other number of minutes. Each event is associated with a time of occurrence during this period. The time of occurrence corresponds to a given phase of a physiological cycle. For example, the breathing cycle repeats every 3-6 seconds. Based on a breathing sensor or data analysis (e.g., variation in TOF data), the breathing cycle is monitored over the period. The cycle is gated or otherwise divided into any number of phases, such as eight. Each event, based on the time of occurrence relative to the cycle, is assigned to a phase. This assignment results in a number (e.g., eight) of sets of TOF data where the TOF data of each set corresponds to a same phase or gate of the cycle. Since the tissue is more likely to be in a same location relative to the detectors at the same phase in the cycle, there is little blurring or motion noise captured by the TOF data for a given phase. The counts or TOF data between phases are subject to motion, so that a LOR and/or location along LOR for one phase does not represent the same tissue as in another phase.

In act 62, the processor corrects the TOF data of the patient for motion in the patient. The correction for a given phase may be the same or different for each bin or TOF data location, so the correction is non-rigid. The correction is locally rigid, but non-rigid across the LORs and/or prompt data.

The histogram image of TOF data for a given phase is non-rigidly corrected based on motion between that phase and a reference phase. The histogram image of TOF data of one phase is motion corrected to the histogram image of TOF data of another phase. For each phase or gate, motion to a reference phase or gate is used to correct. For example, TOF data for gates 1-7 are motion corrected to TOF data for gate 8. The motion fields between each of gates 1-7 to gate 8 are used to correct the TOF data of gates 1-7 to gate 8.

The motion as projected into the TOF domain is applied to the TOF data. A nearest neighbor interpolation is used to motion correct the TOF data. The motion for given LOR and time in one gate relative to another gate gives the LOR and time to which that event from the one gate is assigned in the other gate. To maintain a same sampling, nearest neighbor interpolation is used to rebin the TOF data for motion correction.

In act 64, the motion correction acts to combine the TOF data from the different phases into one data set of events or counts. The forward projected motion vector fields for different gates are used to determine the bin for the reference gate. By reassigning from the different gates to the reference gate, the TOF data are combined. All of the events from the different gates are combined into one set. In alternative embodiments, less than all the TOF data are combined, such as combining counts from two phases together but not from other phases. The motion correction in the projection domain allows combination of the histogram images of the TOF data from the different phases into a single histogram image or into a fewer number of histogram images. The coordinates or bin in projection space of the TOF data for one or more phases are transformed to coordinates or bins in projection space of the TOF data for the reference phase. The TOF data is rebinned. The forward projection of the motion vector fields relates the projection coordinates or bins between phases.

The projection data (TOF data) and image in the object space are discretely sampled. Equidistant sampling in the radial, TOF (i.e., time or position along the LOR), and axial coordinates is used. r, t, and z are discrete indices. To preserve Poisson statistics, which are discrete, detected counts are combined from projection bins of various gates to one particular target gate projection data bin. In other words, the motion matrix M is approximated as a bin-to-bin assignment, defined by the nearest neighbor approximation of M elements in terms of motion vector $d^m$, which is discretely sampled in image space as well, from the target image to each gate image m. Therefore, measured prompt counts y are combined according to:

$$y_{rtz}^{MC} = \sum_m \sum_{r't'z'} \delta_{[r+d_r^m(r,t,z)][t+d_t^m(r,t,z)][z+d_z^m(r,t,z)],r't'z'} y_{r't'z'}^m, \quad (8)$$

where [ ] is a rounding operator, and the Kronecker delta, δ, maps a bin from the m gate projection into the target gate projection data bin. In this "pull" method, coordinates of the target histo-image are translated to coordinates in the warped histo-image and the histo-image's nearest bin point is pulled to assemble data.

Figure 4A:
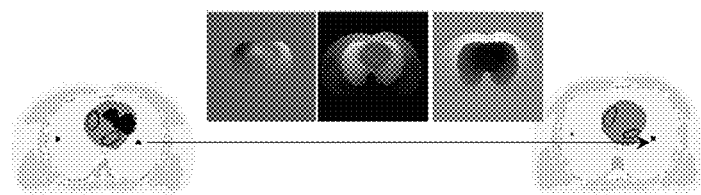
FIG. 4A illustrates an example of image-based motion correction.
Figure 4A:
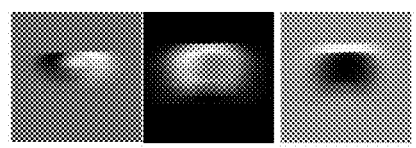
Figure 4B:
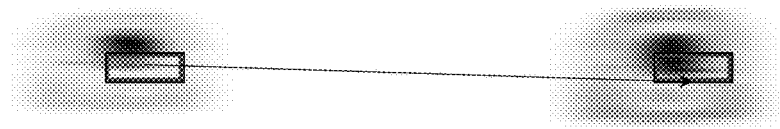
FIG. 4B illustrates an example of motion correction in the TOF domain.

FIGS. 4A and 4B schematically represent motion correction procedures. FIG. 4A shows image-based motion correction. The counts for the different gates are separately reconstructed into the target space and the motion in the target or tissue space is applied to the images. The voxel of a target image is "pulling" values from the other gate images. Three images above the arrow are x, y, and z motion images. FIG. 4B shows a similar procedure, but in the TOF domain. The images representing TOF and motion images are blurred and down-sampled according to the TOF model. TOF blurring is applied in the horizontal direction in this case. Since the data is in the TOF domain, blurring results from the lack of reconstruction.

The nearest neighbor interpolation may potentially produce empty projection bins in the motion-corrected gate data. Since projection data of warped gates are combined with target gate data, such gaps are eventually filled.

The bins may not be sampled equidistantly in the radial direction. An additional transition from the radial position into LOR indices is employed during the combination of data for use in reconstruction.

In act 65, the normalization and/or attenuation are corrected for motion. Due to the summation law of Poisson statistics (assuming that the TOF mean data of m gate projection data and target projection data are the same), motion-corrected data normalization and attenuation factors are computed as:

$$\varepsilon_{rtz}^{MC} = \sum_m \sum_{r't'z'} \delta_{[r+d_r^m(r,t,z)][t+d_t^m(r,t,z)][z+d_z^m(r,t,z)],r't'z'} \varepsilon_{r't'z'}^m a_{r'z'}^m. \quad (9)$$

Post normalization of combined data may minimize noise. Attenuation, a, is motion-dependent since the attenuation map underwent a non-rigid transformation and attenuation is global (TOF independent factor). In fact, both efficiency (normalization inverse) ε and attenuation a are of non-TOF distribution. The motion-corrected combined efficiency is, however, TOF-dependent. The final image reconstruction is performed from the combined measured data, which are modeled as $\varepsilon_{rtz}^{MC} p_{rtz} + b_{rtz}$. Background counts, b, are a combination of scatter and mean randoms events. The scatter component may be modeled according to the targeted gate image. A mean random estimation may be combined from the estimated mean randoms of each gate in a manner similar to that of equation (8). The delta function is used to motion correct the normalization and/or attenuation factors.

In act 66, the processor reconstructs an image from the combined TOF data from the plurality of phases. The activity distribution is reconstructed from the motion corrected TOF data. The combined counts as rebinned with motion correction are used to reconstruct. The activity distribution in an object space of the tissue is reconstructed from the combined TOF data. Due to the combination, a greater number of counts are available for the reconstruction. Rather than dedicating the processing to separately reconstructing for each phase or gate, a single or fewer number of reconstructions are performed due to the motion correction applied in the TOF domain. Rather than using the motion as a constraint in the iteration loop of reconstruction, the motion correction is applied to provide the initial data used for reconstruction. The object space is reconstructed form the PET TOF, such as from prompt data. The activity distribution in three-dimensions is reconstructed. The activity distribution is used for imaging, such as volume rendering, multi-planar reconstruction, or planar imaging.

Any reconstruction may be used. In one embodiment, the reconstruction is an OSEM reconstruction. A Poisson iterative reconstruction, such as maximum likelihood reconstruction, FORE, or other reconstructions may be used. The reconstruction estimates the object or patient space from the LORs. The detected events are used to iteratively determine the object space using forward and backward projection.

The reconstruction may account for the TOF motion correction. TOF-dependent normalization, as a result of equation (9), is used. The reconstruction is performed using the motion corrected normalization and/or attenuation.

In act 68, a PET image is displayed. The reconstructed activity or emission distribution is used to create the PET image. An image is reconstructed by reconstructing the object space and then rendering or imaging from the reconstructed object. The image is of the patient, such as a PET image showing function or uptake of the radiopharmaceutical.

Motion correction applied to TOF data, motion correction applied to images after reconstruction, and no motion correction are compared using simulation. Initial results show that motion correction applied in the projection domain accommodates for changes in non-rigid body movements for a typical (e.g., breathing) pattern of patient motion.

An XCAT phantom is used in the computer simulations. The TOF PET data and attenuation factors are created using Siemens mCT scanner specifications. Eight gate images, both attenuation maps and activity images, are produced along with motion vector fields from one gate image (i.e., the target image for reconstruction) to the rest of the gates images. The significant respiratory motion of up to about 1.6 cm magnitude is simulated in the activity and attenuation images. For the reconstructions, any number of iterations and/or any stop criterion may be used. For example, up to ten iterations are computed, and 21 subsets of azimuthal views are used. As example, mCT has 168 views, and 21 subsets are used so each subset has 8 views. The subsets are used sequentially in one iteration.

FIGS. 5A-H show object space or activity images reconstructed from TOF data representing or grouped into different gates in the simulation of the XCAT phantom. Six spherical hot spots (8 mm diameter) are inserted in the lung region, and the recovery in the reconstructed image serves as the figure of merit in the comparison of the motion correction methods. FIGS. 5A-D images correspond to the target or reference gate image (gate #1). FIG. 5A represents axial slice 55, FIG. 5B represents axial slice 65, and FIG. 5C represents axial slice 79. FIG. 5E-H show images corresponding to gate #5. FIG. 5E shows axial slice 47, FIG. 5F shows axial slice 60, and FIG. 5G shows axial slice 74 axial slices. The axial slices were chosen to show the hot spots, so the different index number indicates motion of the hot spots between the gates. FIG. 5D is a coronal view for gate #1, and FIG. 5H is a coronal view for gate #5. The transaxial images show six inserted hot spots and their relocation from one gate image to another gate image. Slice index increased from the bottom to top of coronal images.

To show improvement provided by greater TOF resolution, simulations are performed with the TOF data at different resolutions. TOF data of 580 ps TOF resolution is simulated with 13 TOF bins. Also, TOF data of 290 ps TOF resolution is simulated with 25 TOF bins. Thirty percent scatter and 50% random fractions are simulated. Added background data are the same for each gate projection data. All gates are considered to be equal in terms of duration of acquisition.

Different amounts of Poisson noise may be added in the simulated data. A low noise data set contains about 240 million true events (unscattered and scattered trues combined). A high noise data set contains about 30 million true events. This noise level is of typical magnitude for patient studies.

The three motion correction approaches are tested. The first approach is gate-by-gate reconstructions (using corresponding attenuation), where the resulting object space images are motion corrected and then combined. The nearest neighbor interpolation (the pull method) is used in the image combination in object space. This relatively easy implementation of motion correction methodology serves as a gold standard and is referred to as "image-based motion correction." The second approach is reconstruction from combined TOF projection data after motion correction in the projection domain and is referred to as TOF motion correction. The third approach is reconstruction from data, simply summed over the gate index, without motion correction and is referred to as "no motion correction." The target image attenuation is used for correction in this case.

FIGS. 6A-D show examples. Using noise free TOF data, image-based motion correction results in images of FIG. 6A being practically equivalent to the original target image, although some blurring may be present since the interpolation is not an inverse operation to the generation of the gate images. The no motion correction image of FIG. 6B has image blurring. A 580 ps TOF motion correction reconstruction is superior to the reconstruction with no motion correction, but the resulting image of FIG. 6C shows noticeable motion artifacts. An increase in TOF data resolution (e.g., 290 ps) results in a TOF motion correction image of FIG. 6D where the mentioned artifacts are well suppressed.

Recovery as a function of noise for the small hot objects in a liver region of interest is tested with low noise TOF data. After ten OSEM iterations, a contrast-noise trade-off results. The motion correction in the projection domain results in better recoveries compared to reconstruction with no motion correction. Better TOF resolution results in similar, except in one hot spot case, recoveries compared to the imaged-based motion correction.

For high noise content of the TOF data, the hot spot recovery with image-based motion correction lowers as noise increases. Recovery is more stable with respect to noise for TOF motion correction and no motion correction.

For cold, but non zero activity, lung spot recoveries, cold spot positive bias occurs in the gold standard image-based motion correction reconstruction. This may explain observed bias in the hot object recoveries.

The TOF motion correction is approximate to non-rigid motion correction. Using nearest neighbor interpolation to preserve data Poisson statistics, it may be more difficult to accommodate mass preservation constraints used in cardiac imaging. Nevertheless, most of the body contains water and this substance is practically non-compressible, so intensity preserved methodology is valid most of the time for whole body imaging.

The robustness of the TOF motion correction increases with better TOF resolution. However, TOF data may be significant in size, and TOF mashing and axial rebinning may be exploited for data compression. More sophisticated data combinations may be used to produce non-TOF data with TOF benefits. The TOF motion correction may be straightforwardly accommodated in such data size reduction algorithms.

Recovery-noise trade-off shows the quicker noise convergence of an imaged-based motion correction. Purely data-based reconstruction algorithms, such as TOF motion correction and no motion correction, show increased noise as iterations proceed. On the other hand, image-based motion correction shows degradation effects, such as bias in cold and hot spots for low count data. This may be expected, since independent gate reconstruction should suffer from bias associated with non-negativity constraint of the ML(OS)-EM reconstruction. Better TOF resolution results in image improvement in image-based motion correction reconstructions, but not in the no motion correction reconstructions.

TOF locality allows for non-rigid motion correction performed in the quasi image (TOF data) space. The image improvement even with the current TOF resolution at about 600 ps is provided as compared to no motion correction. Improved motion correction occurs with better TOF resolution. This TOF motion correction may be useful in faster reconstruction from the Poisson model preserved data as compared to image-based motion correction.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for motion correction in time-of-flight positron emission tomography, the method comprising:
    acquiring, from a memory, a motion vector field for motion of tissue of a patient over a plurality of phases of a physiological cycle;
    acquiring, with a positron emission tomography (PET) scanner having a plurality of detectors, time of flight data along lines-of-response from emissions, the time of flight data being in a plurality of sets for the respective plurality of phases;
    forward projecting the motion vector field along at least one dimension;
    combining the time of flight data for the plurality of phases as a function of the forward projection of the motion vector field;
    reconstructing an image from the combined time of flight data from the plurality of phases; and
    displaying the image.

2. The method of claim 1 wherein acquiring the motion vector field comprises acquiring from magnetic resonance imaging.

3. The method of claim 1 wherein acquiring the motion vector field comprises acquiring as the motion vector field along three Cartesian coordinates, wherein forward projecting comprises forward projecting along the three Cartesian coordinates, and further comprising converting the forward projections along the three Cartesian coordinates into a radial coordinate, time, and axial coordinate of the time of flight data.

4. The method of claim 1 wherein acquiring the time of flight data comprises acquiring projection data along lines of response with a time coordinate.

5. The method of claim 1 wherein acquiring the time of flight data comprises acquiring first counts for a first of the plurality of phases and second counts for a second of the plurality of phases, the second counts subject to the motion of the tissue relative to the first counts, the motion represented in the motion vector field.

6. The method of claim 1 wherein forward projecting comprises forward projecting into a projection space of the time of flight data before reconstruction.

7. The method of claim 1 wherein forward projecting comprises integrating in an object space of the tissue into a projection space along lines of response.

8. The method of claim 1 wherein combining comprises rebinning the time of flight data for one or more of the plurality of phases to a reference one of the plurality of phases with the forward projection of the motion vector field relating bins of the time of flight data for the one or more of the plurality of phases to bins of the reference one of the plurality of phases.

9. The method of claim 8 wherein rebinning comprises performing a nearest neighbor interpolation.

10. The method of claim 1 wherein combining comprises translating coordinates in projection space of the time of flight data for a first phase of the plurality of phases to coordinates in projection space of the time of flight data for a second phase of the plurality of phases.

11. The method of claim 1 wherein combining comprises combining histo-images of the time of flight data from the plurality of phases into a single histo-image.

12. The method of claim 1 wherein reconstructing comprises determining an activity distribution in an object space of the tissue from the combined time of flight data.

13. The method of claim 1 wherein displaying the image comprises displaying a PET image.

14. The method of claim 1 further comprising motion correcting normalization and attenuation; and wherein reconstructing comprises reconstructing as a function of the motion corrected normalization and attenuation.

15. A non-transitory computer readable storage medium having stored therein data representing instructions executable by a programmed processor for motion correction in time-of-flight positron emission tomography (PET), the storage medium comprising instructions for:
  correcting time of flight data of a patient for motion of the patient, wherein correcting time of flight data further comprises:
  acquiring, from a memory, a motion vector field for motion of tissue of a patient over a plurality of phases of a physiological cycle;
  acquiring, with a PET scanner having a plurality of detectors, time of flight data along lines-of-response from emissions, the time of flight data being in a plurality of sets for the respective plurality of phases;
  forward projecting the motion vector field along at least one dimension;
  combining the time of flight data for the plurality of phases as a function of the forward projection of the motion vector field;
  reconstructing an activity distribution from the motion corrected time of flight data; and
  displaying a positron emission tomography image as a function of the activity distribution.

16. The non-transitory computer readable storage medium of claim 15 wherein correcting comprises non-rigidly correcting the time of flight data of a first histogram representing detected emissions at first phase of a physiological cycle to the time of flight data of a second histogram representing detected emissions at a second phase of the physiological cycle.

17. The non-transitory computer readable storage medium of claim 15 wherein correcting comprises correcting the time of flight data as locally rigid.

18. The non-transitory computer readable storage medium of claim 15 further comprising correcting normalization and attenuation for the motion.

19. A system for motion correction in time-of-flight positron emission tomography (PET), the system comprising:
  rings of detectors spaced axially configured to perform a PET scan along lines of response between the detectors;
  a coincidence processor configured to detect the lines of response and time of flight for events acquired from the PET scan, wherein the events are gated into different phases of a physiological cycle, and wherein the motion correction accounts for motion between the phases with the motion forward projected into an event domain; and
  a processor configured to apply motion correction to data representing the detection of the lines of response and time of flight and to reconstruct an activity distribution from the motion corrected data.

* * * * *